United States Patent
Kang et al.

(10) Patent No.: US 8,288,146 B2
(45) Date of Patent: Oct. 16, 2012

(54) SALMONELLA BACTERIOPHAGE AND ANTIBACTERIAL COMPOSITION COMPRISING THE SAME

(75) Inventors: In Hye Kang, Suwon-si (KR); Min Tae Park, Seoul (KR); Young Wook Cho, Seoul (KR); Soo An Shin, Seoul (KR); Hyang Choi, Anyang-si (KR)

(73) Assignee: CJ Cheiljedang Corporation, Seoul (KR)

( * ) Notice: Subject to any disclaimer, the term of this patent is extended or adjusted under 35 U.S.C. 154(b) by 246 days.

(21) Appl. No.: 12/560,263

(22) Filed: Sep. 15, 2009

(65) Prior Publication Data

US 2010/0158870 A1 Jun. 24, 2010

(30) Foreign Application Priority Data

Dec. 24, 2008 (KR) .................. 10-2008-0133909

(51) Int. Cl.
*C12N 7/00* (2006.01)

(52) U.S. Cl. .................................... 435/235.1

(58) Field of Classification Search .................. None
See application file for complete search history.

(56) References Cited

U.S. PATENT DOCUMENTS

| 6,485,902 B2 | 11/2002 | Waddell et al. |
| 6,942,858 B1 | 9/2005 | Ghanbari et al. |
| 2004/0208853 A1* | 10/2004 | Sulakvelidze et al. ....... 424/93.6 |

OTHER PUBLICATIONS

O'Flynn et al., Journal of Applied Microbiology, 2006, 101:251-259.*
Barrangou et al., Applied and Environmental Microbiology, 2002, 68(11):5452-5458.*
Goto et al., J. Food Hyg. Soc. Japan, 2004, 45(1):25-28.*

* cited by examiner

*Primary Examiner* — Zachariah Lucas
*Assistant Examiner* — Nicole Kinsey White
(74) *Attorney, Agent, or Firm* — Knobbe, Martens, Olson & Bear, LLP

(57) ABSTRACT

The present invention relates to a novel bacteriophage, more particularly, a bacteriophage that has a specific bactericidal activity against *Salmonella typhimurium, Salmonella gallinarum,* or *Salmonella pullorum,* a composition for the prevention or treatment of infectious diseases including salmonellosis and *Salmonella* food poisoning caused by *Salmonella typhimurium,* Fowl typhoid caused by *Salmonella gallinarum,* and Pullorum disease caused by *Salmonella pullorum,* which comprises the bacteriophage as an active ingredient, and an animal feed, drinking water, cleaner, and sanitizer which comprise the bacteriophage as an active ingredient.

8 Claims, 7 Drawing Sheets

[Figure 1]
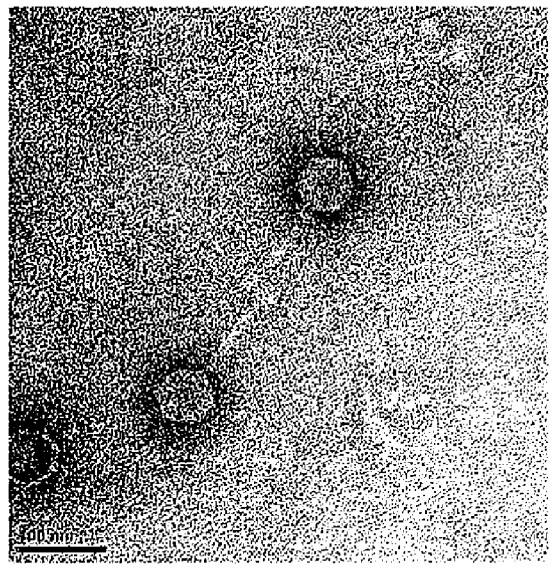
[Figure 2]
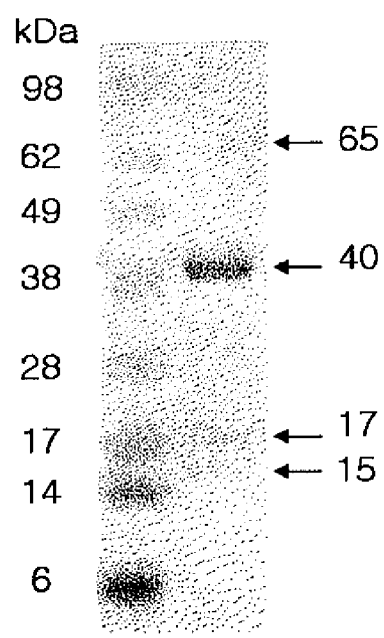

[Figure 3]
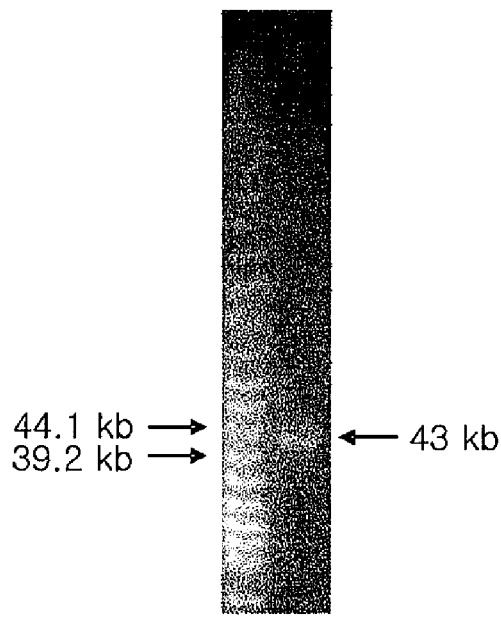
[Figure 4]
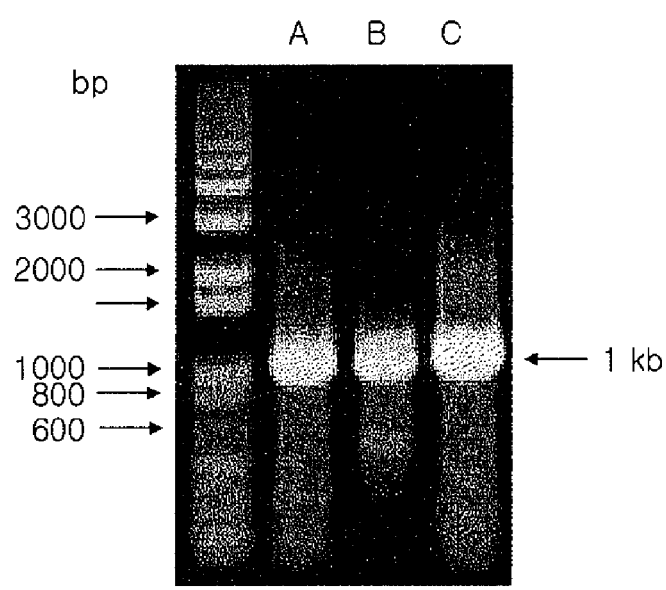

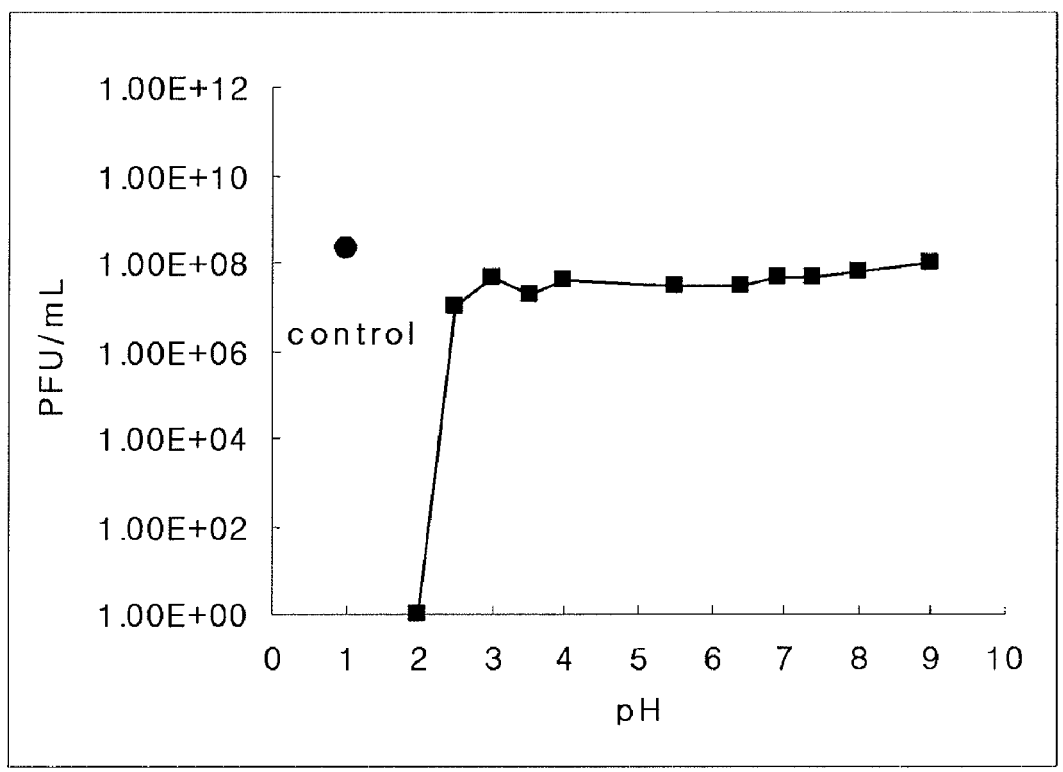
[Figure 5]

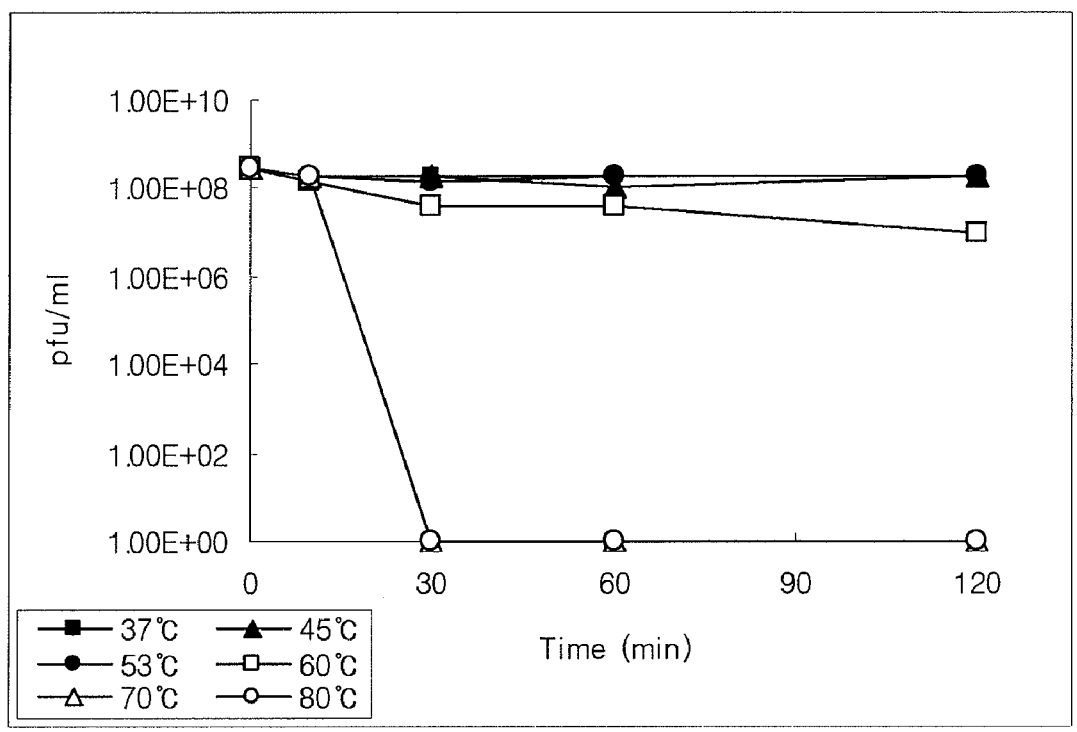
[Figure 6]

[Figure 7]
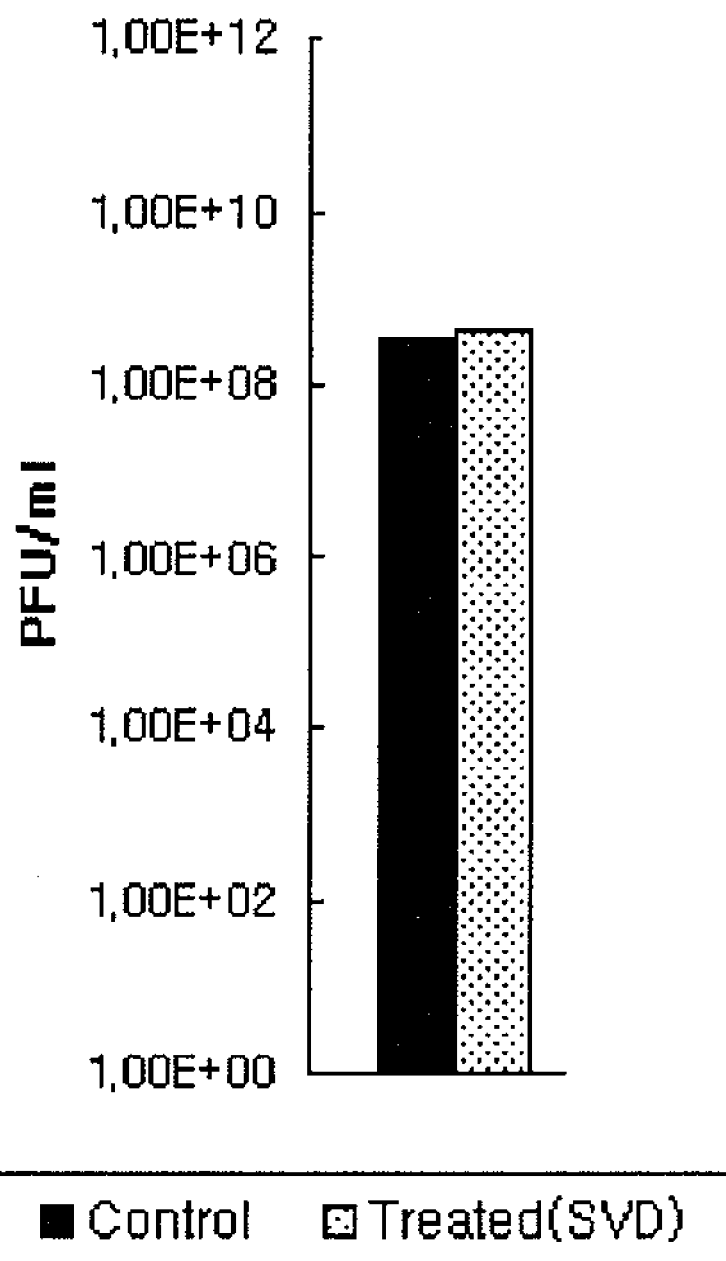

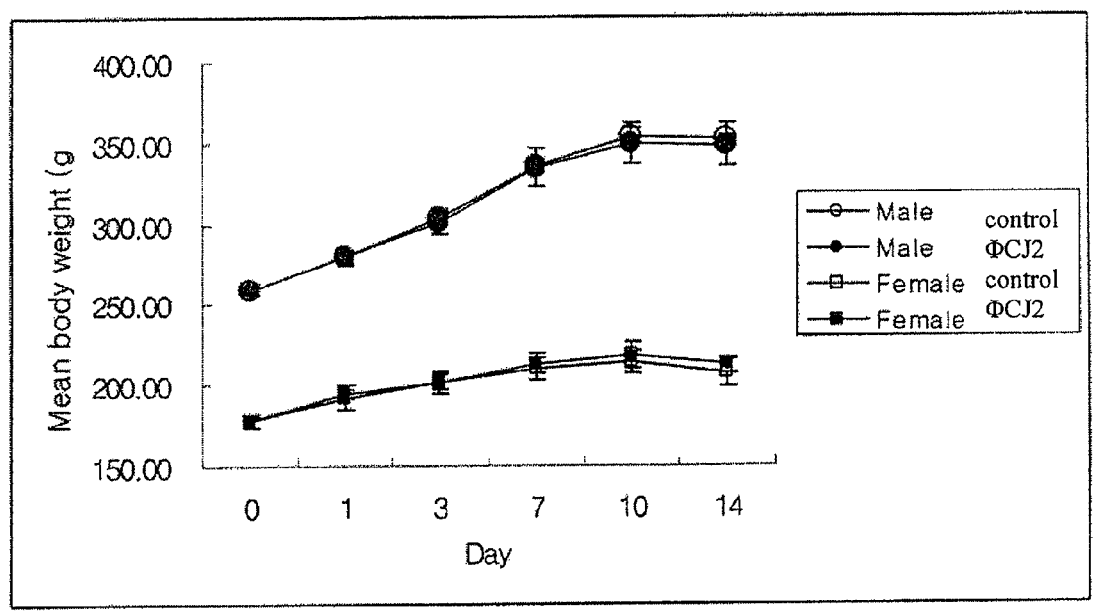
[Figure 8]

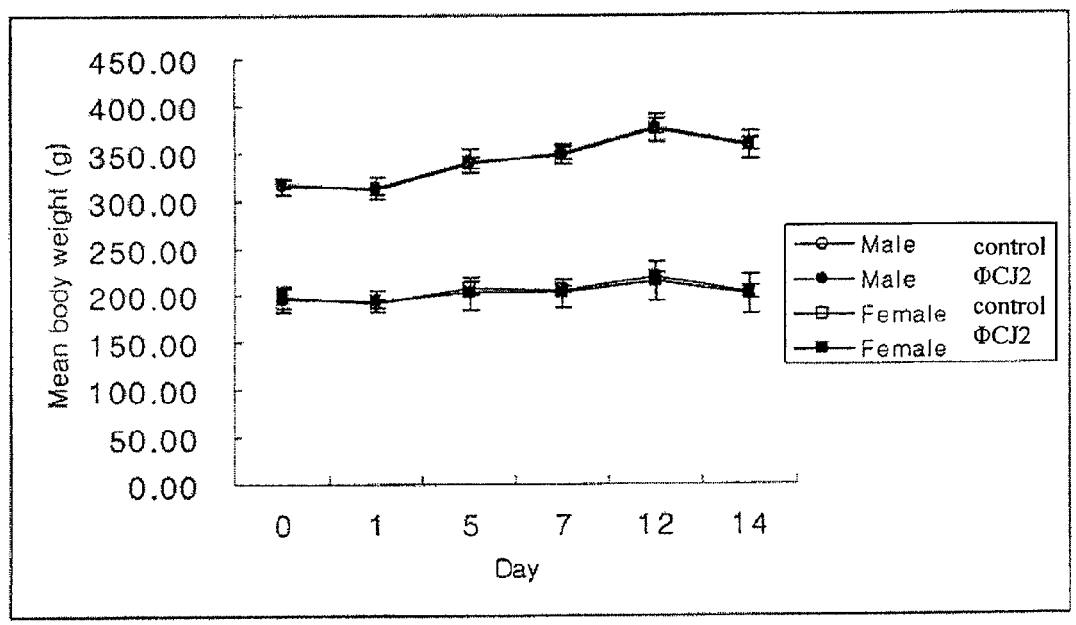
[Figure 9]

SALMONELLA BACTERIOPHAGE AND ANTIBACTERIAL COMPOSITION COMPRISING THE SAME

This application claims the benefit of Korea Patent Application Number 10-2008-0133909 filed on Dec. 24, 2008, the disclosure of which is hereby expressly incorporated by reference in its entirety and hereby expressly made a portion of this application.

TECHNICAL FIELD

The present invention relates to a novel bacteriophage, more particularly, a bacteriophage that has a specific bactericidal activity against *Salmonella typhimurium, Salmonella gallinarum,* or *Salmonella pullorum*, a composition for the prevention or treatment of infectious diseases including salmonellosis and *Salmonella* food poisoning caused by *Salmonella typhimurium*, Fowl typhoid caused by *Salmonella gallinarum*, and Pullorum disease caused by *Salmonella pullorum*, which comprises the bacteriophage as an active ingredient, and an animal feed, drinking water, cleaner, and sanitizer which comprise the bacteriophage as an active ingredient.

BACKGROUND ART

*Salmonella* is a genus of the family Enterobacteriaceae, characterized as Gram-negative, facultatively anaerobic, non spore-forming, rod-shaped bacteria, and most strains are motile by flagella. *Salmonella* has an average genome GC content of 50-52%, which is similar to those of *Escherichia coli* and *Shigella*. The genus *Salmonella* is a pathogenic microorganism that causes infections in livestock as well as in human. *Salmonella enterica*, a species of *Salmonella* bacterium, has a variety of serovars including *Gallinarum, Pullorum, Typhimurium, Enteritidis, Typhi, Choleraesuis,* and *derby* (Bopp C A, Brenner F W, Wells J G, Strokebine N A. *Escherichia, Shigella, Salmonella*. In Murry P R, Baron E J, et al eds Manual of clinical Microbiology. 7th ed. Washington D.C. American Society for Microbiology 1999; 467-74; Ryan K J. Ray C G (editors) (2004). Sherris Medical Microbiology (4th ed). McGraw Hill. ISBN 0-8385-8529-9). Of them, *Salmonella Gallinarum* and *Pullorum* are fowl-adapted pathogens, *Salmonella Typhi* is a human-adapted pathogen, *Salmonella Choleraesuis* and *derby* are swine-adapted pathogens, and *Salmonella Enteritis* and *Typhimurium* are pathogenic for both human and animals. Each serovar causes illness in that species, resulting in serious negative effects for farmers or consumers.

A disease of domestic birds, caused by *Salmonella* bacterium is Fowl Typhoid (FT), which is caused by a pathogen, *Salmonella Gallinarum* (hereinbelow, designated as SG). Fowl Typhoid (FT) is a septicemic disease of domestic birds such as chicken and turkey, and the course may be acute or chronic with high mortality. Recently, it has been reported that Fowl Typhoid frequently occurs in Europe, South America, Africa, and South-East Asia, and damages are increasing. Outbreaks of FT in Korea have been reported since 1992 and economic losses from FT in brown, egg-laying chickens are very serious (Kwon Yong-Kook. 2000 annual report on avian diseases. Information publication by National Veterinary Research & Quarantine Service. March, 2001; Kim Ae-Ran et al., The prevalence of pullorum disease-fowl typhoid in grandparent stock and parent stock in Korea, 2003, Korean J Vet Res (2006) 46(4): 347~353).

Pullorum disease is also caused by one of *Salmonella* bacteria, *Salmonella Pullorum* (hereinbelow, designated as SP). Pullorum disease occurs in any age or season, but young chickens are particularly susceptible to the disease. During the past century, Pullorum disease as an egg-transmitted infection has seriously affected young chickens at 1-2 weeks of age or younger in the world and Korea. In the 1980's, disease occurrence greatly decreased. However, incidence began increasing in the mid 1990's (Kwon Yong-Kook. 2000 annual report on avian diseases. Information publication by National Veterinary Research & Quarantine Service. March, 2001; Kim Ae-Ran et al., The prevalence of pullorum disease-fowl typhoid in grandparent stock and parent stock in Korea, 2003, Korean J Vet Res (2006) 46(4): 347-353).

In Korea, outbreaks of Fowl Typhoid and Pullorum disease have been increasing since the 1990's, inflicting economic damages on farmers. For this reason, a live attenuated SG vaccine has been used in broilers for the prevention of Fowl Typhoid from 2004 (Kim Ae-Ran et al., The prevalence of pullorum disease-fowl typhoid in grandparent stock and parent stock in Korea, 2003, Korean J Vet Res (2006) 46(4): 347-353), even though its efficacy is doubtful, and the live vaccine is not allowed to be used for layers because of the risk of egg-transmitted infections. Unfortunately, there are still no commercially available preventive strategies against Pullorum disease, unlike Fowl Typhoid. Thus, there is an urgent need for new ways to prevent Fowl Typhoid and Pullorum disease.

Meanwhile, *Salmonella Typhimurium* (hereinbelow, designated as ST) is a zoonotic pathogen which shows no host specificity, unlike SG or SP (Zoobises Report; United Kingdom 2003).

ST is a cause of salmonellosis in poultry, pigs, and cattle, etc. Salmonellosis is caused by Salmonella bacteria, an acute or chronic infection of the digestive tract in livestock, and shows the major symptoms of fever, enteritis, and septicemia, occasionally pneumonia, arthritis, abortion, and mastitis. Salmonellosis occurs worldwide, and most frequently during the summer months (T. R. Callaway et al. Gastrointestinal microbial ecology and the safety of our food supply as related to Salmonella. J Anim Sci 2008.86:E163-E172). In cattle, typical symptoms include loss of appetite, fever, dark brown diarrhea or bloody mucous stool. Acute infection in calves leads to rapid death, and infection during pregnancy leads to fetal death due to septicemia, resulting in premature abortion. In pigs, salmonellosis is characterized clinically by three major syndromes—acute septicemia, acute enteritis, and chronic enteritis. Acute septicemia occurs in 2~4 month-old piglets, and death usually occurs within 2~4 days after onset of symptoms. Acute enteritis occurs during the fattening period, and is accompanied by diarrhea, high fever, pneumonia, and nervous signs. Discoloration of the skin may occur in some severe cases. Chronic enteritis is accompanied by continuing diarrhea.

Once an outbreak of salmonellosis occurs in poultry, pigs, and cattle, it is difficult to halt with therapeutic agents. The reasons are that *Salmonella* bacteria exhibit a strong resistance to various drugs and live in cells being impermeable to antibiotics. Up to now, there have been no methods for effectively treating salmonellosis caused by ST, including antibiotics.

In addition to livestock, ST causes infections in human via livestock products, leading to salmonella food poisoning. Consumption of infected, improperly cooked livestock products (e.g., meat products, poultry products, eggs and by-products) is a cause of human infection. *Salmonella* food poisoning in human usually involves the prompt onset of headache, fever, abdominal pain, diarrhea, nausea, and vomiting. The symptoms commonly appear within 6-72 hours after the ingestion of the organism, and may persist for as long as 4-7 days or even longer (NSW+HEALTH. Jan. 14, 2008).

According to a report by the CDC (The Centers for Disease Control and Prevention, USA), 16% of human food poisoning outbreaks between 2005 and 2008 attributed to Salmonella bacteria, and 18% of them were ST (*Salmonella Typhimurium*). With respect to salmonella food poisoning in human between 1973 and 1984, the implicated food vehicles of transmission were reportedly chicken (5%), beef (19%), pork (7%), dairy products (6%), and turkey (9%). In 1974~1984, the bacterial contamination test on broilers during the slaughter process showed 35% or more of *salmonella* incidence. In 1983, salmonella was isolated in 50.6% of chicken, 68.8% of turkey, 60% of goose, 11.6% of pork, and 1.5% of beef. Further, a survey carried out in 2007 reported that *salmonella* was found in 5.5% of raw poultry meat and 1.1% of raw pork. In particular, it was revealed that ST commonly originated from contaminated pork, poultry meat, and beef (www.cdc.gov (Centers for Disease Control and Prevention (CDC)). A risk assessment conducted by FAO and WHO in 2002 noted that the human incidence of salmonellosis transmitted through eggs and poultry meat appeared to have a linear relationship to the observed *Salmonella* prevalence in poultry. This implies that, by reducing the prevalence of *Salmonella* in poultry, the incidence of salmonellosis in humans will correspondingly fall (*Salmonella* control at the source; World Health Organization. International Food Safety Authorities Network (INFOSAN) Information Note No. March 2007). Recently, fears about food safety have been spurred by outbreaks of salmonella from products as varied as peanuts, spinach, tomatoes, pistachios, peppers and, most recently, cookie dough (Jane Black and Ed O'Keefe. Overhaul of Food Safety Rules in the Works. Washington Post Staff Writers Wednesday, Jul. 8, 2009).

For these reasons, *Salmonella* infections must be reported in Germany (§6 and §7 of the German law on infectious disease prevention, Infektionsschutzgesetz). Between 1990 and 2005 the number of officially recorded cases decreased from approximately 200,000 cases to approximately 50,000. It is estimated that every fifth person in Germany is a carrier of Salmonella. In the USA, there are approximately 40,000 cases of *Salmonella* infection reported each year.

Therefore, there is an urgent need to control ST, which causes salmonellosis in livestock and human. The collaborative efforts of USDA and FDA have led to the development of a number of effective strategies to prevent salmonellosis that causes over 1 million cases of foodborne illness in the United States. In Denmark, conservative estimates from a cost benefit analysis comparing *Salmonella* control costs in the production sector with the overall public health costs of salmonellosis suggest that *Salmonella* control measures saved the Danish society US$ 14.1 million in the year 2001 (*Salmonella* control at the source. World Health Organization. International Food Safety Authorities Network (INFOSAN) Information Note No. March 2007).

Meanwhile, a bacteriophage is a specialized type of virus that only infects and destroys bacteria, and can self-replicate only inside a host bacteria. A bacteriophage consists of genetic material being single or double-stranded DNA or RNA surrounded by a protein shell. There are three basic structural forms of bacteriophage: an icosahedral (twenty-sided) head with a tail, an icosahedral head without a tail, and a filamentous form. Bacteriophages are classified based on their morphological structure and genetic material. Based on their tail structure, bacteriophages having an icosahedral head and double-stranded, linear DNA as their genetic material are divided into three families: Myoviridae, Siphoviridae, and Podoviridae, which are characterized by contractile, long noncontractile, and short noncontractile tails, respectively. Bacteriophages having an icosahedral head without a tail and RNA or DNA as their genetic material are divided based on their head shape and components, and the presence of a shell. Filamentous bacteriophages having DNA as their genetic material are divided based on their size, shape, shell, and filament components (H. W. Ackermann. Frequency of morphological phage descriptions in the year 2000; Arch Virol (2001) 146:843-857; Elizabeth Kutter et al. Bacteriophages biology and application; CRC press).

During infection, a bacteriophage attaches to a bacterium and inserts its genetic material into the cell. After this a bacteriophage follows one of two life cycles, lytic or lysogenic. Lytic bacteriophages take over the machinery of the cell to make phage components. They then destroy or lyse the cell, releasing new phage particles. Lysogenic bacteriophages incorporate their nucleic acid into the chromosome of the host cell and replicate with it as a unit without destroying the cell. Under certain conditions, lysogenic phages can be induced to follow a lytic cycle (Elizabeth Kutter et al. Bacteriophages biology and application. CRC press).

After the discovery of bacteriophages, a great deal of faith was initially placed in their use for infectious-disease therapy. However, when broad spectrum antibiotics came into common use, bacteriophages were seen as unnecessary because of having a specific target spectrum. Nevertheless, the misuse and overuse of antibiotics resulted in rising concerns about antibiotic resistance and harmful effects of residual antibiotics in foods (Cislo, M et al. Bacteriophage treatment of suppurative skin infections. Arch Immunol. Ther. Exp. 1987. 2:175-183; Kim sung-hun et al., Bacteriophage; New Alternative Antibiotics. biological research information center, BRIC). In particular, antimicrobial growth promoters (AGPs), added to animal feed to enhance growth, is known to induce antibiotic resistance, and therefore, a ban on the use of AGPs has been recently introduced. In the European Union, the use of all antimicrobial growth promoters (AGPs) was banned from 2006. Korea has banned the use of some AGPs from 2009, and is considering restrictions on the use of all AGPs by 2013~2015.

These growing concerns about the use of antibiotics have led to a resurgence of interest in bacteriophage as an alternative to antibiotics. 7 bacteriophages for control of *E. coli* O157:H are disclosed in U.S. Pat. No. 6,485,902 (applied in 2002—Use of bacteriophages for control of *Escherichia coli* O157). 2 bacteriophages for control of various microorganisms are disclosed in U.S. Pat. No. 6,942,858 (applied by Nymox in 2005). Many companies have been actively trying to develop various products using bacteriophages. EBI food system (Europe) developed a food additive for preventing food poisoning caused by *Listeria monocytogenes*, named Listex-P100, which is the first bacteriophage product approved by the US FDA. A phage-based product, LMP-102 was also developed as a food additive against *Listeria monocytogenes*, approved as GRAS (Generally regarded as safe). In 2007, a phage-based wash produced by OmniLytics was developed to prevent *E. coli* O157 contamination of beef during slaughter, approved by USDA's Food Safety and Inspection Service (FSIS). In Europe, *Clostridium sporogenes* phage NCIMB 30008 and *Clostridium tyrobutiricum* phage NCIMB 30008 were registered as a feed preservative against *Clostridium* contamination of feed in 2003 and 2005, respectively. Such studies show that research into bacteriophages for use as antibiotics against zoonotic pathogens in livestock products is presently ongoing.

However, most of the phage biocontrol studies have focused on the control of *E. coli, Listeria*, and *Clostridium*. *Salmonella* is also a zoonotic pathogen, and damages due to this pathogen are significant. As mentioned above, since ST has a multiple drug resistance, nationwide antimicrobial resistance surveillance has been conducted in Korea under an Enforcement Decree of the Act on the Prevention of Contagious Disease (Executive Order 16961), an Enforcement ordinance of the Act on the Prevention of Contagious Disease (Ministry of Health and Welfare's Order 179), and Organization of the National Institute of Health (Executive Order 17164). Accordingly, there is a need for the development of bacteriophages to control *Salmonella*.

DISCLOSURE

Technical Problem

In order to solve the problems including antibiotic resistance due to the misuse and overuse of antibiotics, harmful effects of residual antibiotics in foods, and the problems generated by the use of broad spectrum antibiotics, the present inventors isolated from natural sources a novel *Salmonella* bacteriophage having a specific bactericidal activity against *Salmonella* which causes major diseases in livestock, and identified its morphological, biochemical, and genetic properties. The present inventors found that the bacteriophage has a specific bactericidal activity against *Salmonella typhimurium* (ST), *Salmonella gallinarum* (SG) and *Salmonella pullorum* (SP) without affecting beneficial bacteria, and excellent acid-, heat- and dry-resistance, and thus can be applied to the compositions that can be used for the prevention or treatment of livestock salmonellosis caused by *Salmonella typhimurium*, *Salmonella* food poisoning caused by contaminated livestock products, and infectious diseases caused by *Salmonella gallinarum* or *Salmonella pullorum*, in particular, Fowl typhoid or Pullorum disease, and to various products to control *Salmonella*, such as animal feed additive and drinking water for livestock, barn sanitizers, and cleaners for meat products, thereby completing the present invention.

Technical Solution

It is an object of the present invention to provide a novel bacteriophage having a bactericidal activity against *Salmonella typhimurium, Salmonella gallinarum* or *Salmonella pullorum*.

It is another object of the present invention to provide a composition for the prevention or treatment of infectious diseases caused by *Salmonella typhimurium, Salmonella gallinarum* or *Salmonella pullorum*, comprising the bacteriophage as an active ingredient, in particular, a composition for the prevention or treatment of the infectious diseases which is used as an antibiotic.

It is still another object of the present invention to provide an animal feed and drinking water, comprising the bacteriophage as an active ingredient.

It is still another object of the present invention to provide a sanitizer and cleaner, comprising the bacteriophage as an active ingredient.

It is still another object of the present invention to provide a method for preventing or treating livestock salmonellosis caused by *Salmonella typhimurium* or *Salmonella* food poisoning caused by contaminated livestock products, using the composition that comprises the bacteriophage as an active ingredient.

It is still another object of the present invention to provide a method for preventing or treating infectious diseases, Fowl Typhoid or Pullorum disease caused by *Salmonella gallinarum* and *Salmonella pullorum*.

Advantageous Effects

The novel bacteriophage of the present invention has a specific bactericidal activity against *Salmonella typhimurium, Salmonella gallinarum*, and *Salmonella pullorum*, and excellent acid-, heat- and dry-resistance. Thus, it can be used for the prevention or treatment of infectious diseases caused by *Salmonella typhimurium, Salmonella gallinarum* or *Salmonella pullorum*, including salmonellosis, *Salmonella* food poisoning, Fowl typhoid or Pullorum disease, and also used for the control of *Salmonella typhimurium, Salmonella gallinarum* and *Salmonella pullorum*.

DESCRIPTION OF DRAWINGS

FIG. 1 is an electron microscopy photograph of ΦCJ2, in which ΦCJ2 belongs to the morphotype of the family Siphoviridae, characterized by isometric capsid and long non-contractile tail;

FIG. 2 is the result of SDS-PAGE of the isolated bacteriophage ΦCJ2, in which protein patterns of the bacteriophage are shown, including a major protein of approximately 40 kDa and other proteins of approximately 65 kDa, 17 kDa, and 15 kDa (See-blue plus 2 prestained-standard (Invitrogen) used as marker);

FIG. 3 is the result of PFGE of the isolated bacteriophage ΦCJ2, showing the total genome size of approximately 43 kbp (5 kbp DNA size standard (Bio-rad) as size marker);

FIG. 4 is the result of PCR, performed using each primer set of ΦCJ2 genomic DNA, in which (A; PCR amplification using primer set of SEQ ID NOs. 4 and 5, B; PCR amplification using primer set of SEQ ID NOs. 6 and 7, C; PCR amplification using primer set of SEQ ID NOs. 8 and 9) each of A, B, and C lanes shows a PCR product of approximately 1 kbp;

FIG. 5 is the result of acid-resistance test on the bacteriophage ΦCJ2, showing the number of surviving bacteriophage at pH 2.1, 2.5, 3.0, 3.5, 4.0, 5.5, 6.4, 6.9, 7.4, 8.0, and 9.0, in which the bacteriophage ΦCJ2 retains its infectivity to pH 2.5, but entirely loses its infectivity at pH 2.1, as compared to control;

FIG. 6 is the result of heat-resistance test on the bacteriophage ΦCJ2, showing the number of surviving bacteriophage at 37, 45, 53, 60, 70, and 80 and a time point of 0, 10, 30, 60, 120 min, in which the bacteriophage ΦCJ2 retains its infectivity even after incubation at 60 for 2 hrs, but entirely loses its infectivity after incubation at 70☐ for 10 min;

FIG. 7 is the result of dry-resistance test on the bacteriophage ΦCJ2, performed at 60☐ for 120 min using a speed vacuum dryer (SVD), in which changes in viral titers before and after drying were compared to examine the relative stability, and the phage's infectivity was shown not to decrease;

FIG. 8 is the result of single dose oral toxicity study of ΦCJ2 in rats, showing changes in body weight (○; male control group treated with the mixed solution of 20 mM Tris-HCl and 2 mM MgCl$_2$, ●; male test group treated with 1×10$^{12}$ pfu of ΦCJ2, ■: female control group treated with the mixed solution of 20 mM Tris-HCl and 2 mM MgCl$_2$, ☐;

female test group treated with 1×10$^{12}$ pfu of ΦCJ2), in which no significant changes in body weight were observed even after 14 days; and FIG. 9 is the result of single dose intravenous toxicity study of ΦCJ2 in rats, showing changes in body weight (○; male control group treated with the mixed solution of 20 mM Tris-HCl and 2 mM MgCl$_2$, ●; male test group treated with 1×10$^{12}$ pfu of ΦCJ2, ■; female control group treated with the mixed solution of 20 mM Tris-HCl and 2 mM MgCl$_2$, □; female test group treated with 1×10$^{12}$ pfu of ΦCJ2), in which no significant changes in body weight were observed even after 14 days.

BEST MODE

In accordance with an aspect, the present invention relates to a novel bacteriophage having a specific bactericidal activity against *Salmonella typhimurium*, *Salmonella gallinarum* or *Salmonella pullorum*.

The bacteriophage of the present invention belongs to the morphotype of the family Siphoviridae, characterized by isometric capsid and long non-contractile tail, and has a total genome size of 43 kbp and a major structural protein with a size of 40 kDa.

Specifically, the bacteriophage of the present invention has the capability of selectively infecting *Salmonella typhimurium*, *Salmonella gallinarum* and *Salmonella pullorum*, namely, species specificity.

The bacteriophage of the present invention genetically has a total genome size of 43 kbp, and may include one or more nucleic acid molecules selected from the group consisting of SEQ ID NOs. 1, 2, and 3 within the entire genome, preferably nucleic acid molecules represented by SEQ ID NOs. 1 to 3 within the entire genome.

When the bacteriophage of the present invention is subjected to PCR using one or more primer sets selected from the group consisting of SEQ ID NOs. 4 and 5, SEQ ID NOs. 6 and 7, and SEQ ID NOs. 8 and 9, each PCR product has a size of approximately 1 kbp. Preferably, when PCR is performed using all of the primer sets, each PCR product has a size of approximately 1 kbp.

As used herein, the term "nucleic acid molecule" encompasses DNA (gDNA and cDNA) and RNA molecules, and the term nucleotide, as the basic structural unit of nucleic acids, encompasses natural nucleotides and sugar or base-modified analogues thereof.

The genome of the bacteriophage of the present invention encodes a major structural protein with a size of 40 kDa.

Further, the bacteriophage of the present invention has the biochemical properties of acid- and heat-resistance, in which it can stably retain its infectivity in a wide range of pH environments from pH 2.5 to pH 9.0, and in a high temperature environment from 37☐ to 60☐. In addition, the bacteriophage of the present invention has dry-resistance to stably maintain its infectivity even after high-temperature drying. Such properties of acid-, heat-, and drying-resistance allow application of the bacteriophage of the present invention under various temperature and pH conditions upon the production of prophylactic or therapeutic compositions for livestock diseases caused by ST, SG and SP or human diseases caused by the contaminated livestock.

The present inventors collected sewage samples at chicken slaughterhouses, and isolated therefrom the bacteriophage of the present invention having a specific bactericidal activity against ST, SG and SP and the above characteristics, which was designated as Bacteriophage ΦCJ2 and deposited at the Korean Culture Center of Microorganisms (361-221, Honje 1, Sudaemun, Seoul) on Dec. 17, 2008 under accession number KCCM10976P.

In accordance with the specific Example of the present invention, the present inventors collected sewage samples at chicken slaughterhouses to isolate bacteriophages that lyse the host cell ST, and they confirmed that the bacteriophages are able to lyse SG and SP, specifically (Table 1). Further, they examined the bacteriophage (ΦCJ2) under electron microscope, and found that it belongs to the morphotype of the family Siphoviridae (FIG. 1).

Further, the protein patterns of the bacteriophage ΦCJ2 were also analyzed, revealing a major structural protein with a size of approximately 40 kDa (FIG. 2).

Furthermore, the total genome size of the bacteriophage ΦCJ2 was also analyzed, revealing that it has a total genome size of approximately 43 kbp (FIG. 3). The results of analyzing its genetic features showed that the bacteriophage includes nucleic acid sequences represented by SEQ ID NOs. 1 to 3 within the total genome (Example 6). Based on these results, genetic similarity with other species was compared. It was found that the bacteriophage showed very low genetic similarity with the known bacteriophages, indicating that the bacteriophage is a novel bacteriophages (Table 2). More particularly, the ΦCJ2-specific primer set, in particular, SEQ ID NOs. 4 and 5, SEQ ID NOs. 6 and 7, and SEQ ID NOs. 8 and 9, was used to perform PCR. Each PCR product was found to have a size of approximately 1 kbp (FIG. 4).

Further, when SG and SP were infected with ΦCJ2, the phage plaques (clear zone on soft agar created by host cell lysis of one bacteriophage) showed the same size and turbidity.

Furthermore, the stability of ΦCJ2 was examined under various temperature and pH conditions, revealing that ΦCJ2 stably maintains its infectivity in a wide range of pH environments from pH 2.5 to pH 9.0 (FIG. 5) and in a high temperature environment from 37☐ to 60☐ (FIG. 6), and even after high-temperature drying at 60☐ for 120 minutes (FIG. 7). These results indicate that the bacteriophage ΦCJ2 of the present invention can be readily applied to various products for the control of *Salmonella*.

In accordance with another aspect, the present invention relates to a composition for the prevention or treatment of infectious diseases caused by one or more selected from the group consisting of *Salmonella typhimurium*, *Salmonella gallinarum* and *Salmonella pullorum*, comprising the bacteriophage as an active ingredient.

In one preferred embodiment, the therapeutic composition may include an antibiotic.

The bacteriophage of the present invention has a specific bactericidal activity against *Salmonella typhimurium*, *Salmonella gallinarum* and *Salmonella pullorum*, and thus can be used for the purpose of preventing or treating diseases that are caused by these bacteria. Preferably, examples of the diseases caused by *Salmonella typhimurium* may include salmonellosis or *Salmonella* food poisoning, examples of the diseases caused by *Salmonella gallinarum* may include Fowl typhoid, and examples of the diseases caused by *Salmonella pullorum* may include Pullorum disease, but are not limited thereto.

As used herein, the term "salmonellosis" refers to symptoms caused by *salmonella* infection, including fever, headache, diarrhea, and vomiting, namely, diseases caused by bacteria of the genus *Salmonella*, which is defined two clinical forms—an acute septicemic form that resembles typhoid fever and an acute gastroenteritis, including enteritis, food poisoning, and acute septicemia.

As used herein, the term "prevention" means all of the actions in which the disease is restrained or retarded by the administration of the composition. As used herein, the term "treatment" means all of the actions in which the disease has taken a turn for the better or been modified favorably by the administration of the composition.

The composition of the present invention comprises ΦCJ2 of $5\times10^2$ to $5\times10^{12}$ pfu/ml, preferably $1\times10^6$ to $1\times10^{10}$ pfu/ml.

The composition of the present invention may additionally include a pharmaceutically acceptable carrier, and be formulated together with the carrier to provide foods, medicines, and feed additives.

As used herein, the term "pharmaceutically acceptable carrier" refers to a carrier or diluent that does not cause significant irritation to an organism and does not abrogate the biological activity and properties of the administered compound. For formulation of the composition into a liquid preparation, a pharmaceutically acceptable carrier which is sterile and biocompatible may be used such as saline, sterile water, Ringer's solution, buffered physiological saline, albumin infusion solution, dextrose solution, maltodextrin solution, glycerol, and ethanol. These materials may be used alone or in any combination thereof. If necessary, other conventional additives may be added such as antioxidants, buffers, bacteriostatic agents, and the like. Further, diluents, dispersants, surfactants, binders and lubricants may be additionally added to the composition to prepare injectable formulations such as aqueous solutions, suspensions, and emulsions, or oral formulations such as pills, capsules, granules, or tablets.

The prophylactic or therapeutic compositions of the present invention may be applied or sprayed to the afflicted area, or administered by oral or parenteral routes. The parenteral administration may include intravenous, intraperitoneal, intramuscular, subcutaneous or topical administration.

The dosage suitable for applying, spraying, or administrating the composition of the present invention will depend upon a variety of factors including formulation method, the mode of administration, the age, weight, sex, condition, and diet of the patient or animal being treated, the time of administration, the route of administration, the rate of excretion, and reaction sensitivity. A physician or veterinarian having ordinary skill in the art can readily determine and prescribe the effective amount of the composition required.

Examples of the oral dosage forms suitable for the composition of the present invention include tablets, troches, lozenges, aqueous or emulsive suspensions, powder or granules, emulsions, hard or soft capsules, syrups, or elixirs. For formulation such as tablets and capsules, useful are a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax. For capsules, a liquid carrier such as lipid may be further used in addition to the above-mentioned compounds.

For non-oral administration, the composition of the present invention may be formulated into injections for subcutaneous, intravenous, or intramuscular routes, suppositories, or sprays inhalable via the respiratory tract, such as aerosols. Injection preparations may be obtained by dissolving or suspending the composition of the present invention, together with a stabilizer or a buffer, in water and packaging the solution or suspension in ampules or vial units. For sprays, such as aerosol, a propellant for spraying a water-dispersed concentrate or wetting powder may be used in combination with an additive.

As used herein, the term "antibiotic" means any drug that is applied to animals to kill pathogens, and is used herein as a general term for antiseptics, bactericidal agents and antibacterial agents. The animals are mammals including human. The bacteriophage of the present invention, unlike the conventional antibiotics, has a high specificity to Salmonella so as to kill the specific pathogens without affecting beneficial bacteria, and does not induce resistance so that its life cycling is comparatively long.

In accordance with one specific embodiment of the present invention, single dose oral and intravenous toxicity studies and toxicity study on normal enteric bacteria were performed to evaluate its safety in rats. When a single dose oral toxicity study was performed at a dose level of $1\times10^{12}$ pfu of ΦCJ2, there were no marked clinical signs or animal death (Tables 4 and 5). When a single dose intravenous toxicity study was performed at a dose level of $1\times10^{12}$ pfu of ΦCJ2, there were also no marked clinical signs or animal death (Tables 6 and 7, and FIG. 9). When a toxicity study on normal enteric bacteria was performed by serial dilution of $1\times10^{11}$ pfu/ml of ΦCJ2, it was found that the growth of enteric bacteria was not inhibited even at a maximum dose of ΦCJ2 (Table 8), indicating its safety.

Further, when SG-infected chicken were fed with feed supplemented with ΦCJ2, the ΦCJ2-treated group showed a significantly higher protection rate than the non-treated group. (Table 9), suggesting that ΦCJ2 has prevention and treatment efficacy on SG infection.

In accordance with still another aspect, the present invention relates to an animal feed or drinking water for livestock, comprising the bacteriophage as an active ingredient.

Feed additive antibiotics used in the fishery and livestock industries are used for the purpose of preventing infections, but lead to an increase in resistant strains of bacteria, and residual antibiotics in livestock products may be ingested by humans, contributing to antibiotic resistance in human pathogens and the spread of diseases. In addition, since there are a variety of feed additive antibiotics, the increasing global emergence of multidrug-resistant strains is a serious concern. Therefore, the bacteriophage of the present invention can be used as a feed additive antibiotic that is more ecologically-friendly and able to solve the above problems.

The bacteriophage of the present invention may be separately prepared as a feed additive, and then added to the animal feed, or directly added to the animal feed. The bacteriophage of the present invention may be contained in the animal feed as a liquid or in a dried form, preferably in a dried powder. The drying process may be performed by air drying, natural drying, spray drying, and freeze-drying, but is not limited thereto. The bacteriophage of the present invention may be added as a powder form in an amount of 0.05 to 10% by weight, preferably 0.1 to 2% by weight, based on the weight of animal feed. The animal feed may also include other conventional additives for the long-term preservation, in addition to the bacteriophage of the present invention.

The feed additive of the present invention can additionally include other non-pathogenic microorganisms. The additional microorganism can be selected from a group consisting of *Bacillus subtilis* that can produce protease, lipase and invertase, *Lactobacillus* sp. strain having an ability to decompose organic compounds and physiological activity under anaerobic conditions, filamentous fungi like *Aspergillus oryzae* (J Animal Sci 43: 910-926, 1976) that increases the weight of domestic animals, enhances milk production and helps digestion and absorptiveness of feeds, and yeast like *Saccharomyces cerevisiae* (J Anim Sci 56:735-739, 1983).

The feed comprising ΦCJ2 of the present invention may include plant-based feeds, such as grain, nut, food byproduct, seaweed, fiber, drug byproduct, oil, starch, meal, and grain byproduct, and animal-based feeds such as protein, mineral, fat, single cell protein, zooplankton, and food waste, but is not limited thereto.

The feed additive comprising ΦCJ2 of the present invention may include binders, emulsifiers, and preservatives for the prevention of quality deterioration, amino acids, vitamins, enzymes, probiotics, flavorings, non-protein nitrogen, silicates, buffering agents, coloring agents, extracts, and oligosaccharides for improving process efficiency, and other feed premixtures, but is not limited thereto.

Further, the supply of drinking water mixed with the bacteriophage of the present invention can reduce the number of Salmonella bacteria in the intestine of livestock, thereby obtaining Salmonella-free livestock.

In accordance with still another aspect, the present invention relates to a sanitizer or a cleaner, comprising the bacteriophage as an active ingredient.

The sanitizer comprising the bacteriophage as an active ingredient can be utilized as a valuable food sanitizer, devoted to food-poisoning prevention. Specifically, in a food industry, it can be used as a food sanitizer or food additive for preventing salmonella infections, and in a livestock industry, it can be also used for the production of *Salmonella*-free livestock. In order to remove *Salmonella*, the sanitizer can be used in sewage disposal plants, and also in poultry barns, slaughterhouses, contaminated areas, and other production facilities, but is not limited thereto.

Further, the cleaner comprising the bacteriophage as an active ingredient can be applied to the contaminated skin, feathers, and other contaminated body parts of living animals, in order to remove *Salmonella*.

In accordance with still another aspect, the present invention relates to a method for treating infectious diseases caused by *Salmonella typhimurium, Salmonella gallinarum* or *Salmonella pullorum*, using the bacteriophage that has a specific bactericidal activity against *Salmonella typhimurium, Salmonella gallinarum*, or *Salmonella pullorum*.

In accordance with still another aspect, the present invention relates to a method for treating infectious diseases caused by *Salmonella typhimurium, Salmonella gallinarum* or *Salmonella pullorum*, using the composition for the prevention or treatment of infectious diseases caused by *Salmonella typhimurium, Salmonella gallinarum* or *Salmonella pullorum*.

The composition of the present invention may be administered to animals in a pharmaceutical formulation or as a component of the animal feed or in their drinking water, preferably administered by mixing into the animal feed as a feed additive.

The composition of the present invention may be administered in a typical manner via any route such as oral or parenteral routes, in particular, oral, rectal, topical, intravenous, intraperitoneal, intramuscular, intraarterial, transdermal, intranasal, and inhalation routes.

The method for treating the diseases of the present invention includes administration of a pharmaceutically effective amount of the composition of the present invention. It will be obvious to those skilled in the art that the total daily dose should be determined through appropriate medical judgment by a physician. The therapeutically effective amount for patients may vary depending on various factors well known in the medical art, including the kind and degree of the response to be achieved, the patient's condition such as age, body weight, state of health, sex, and diet, time and route of administration, the secretion rate of the composition, the time period of therapy, concrete compositions according to whether other agents are used therewith or not, etc.

Hereinafter, the present invention will be described in more detail with reference to the following Examples. However, these Examples are for illustrative purposes only, and the invention is not intended to be limited by these Examples.

MODE FOR INVENTION

Example 1

*Salmonella* Bacteriophage Isolation 1-1. Bacteriophage Screening and Single Bacteriophage Isolation 50 ml of sample from chicken slaughterhouse and sewage effluent was transferred to a centrifuge tube, and centrifuged at 4000 rpm for 10 minutes. Then, the supernatant was filtered using a 0.45 μm filter. 18 ml of sample filtrate was mixed with 150 μl of ST shaking culture medium ($OD_{600}$=2) and 2 ml of 10× Luria-Bertani medium (Hereinbelow, designated as LB medium, tryptone 10 g; yeast extract 5 g; NaCl 10 g; final volume to 1 L). The mixture was cultured at 37□ for 18 hours, and the culture medium was centrifuged at 4000 rpm for 10 minutes. The supernatant was filtered using a 0.2 μm filter. 3 ml of 0.7% agar (w/v) and 150 μl of ST shaking culture medium ($OD_{600}$=2) were mixed, and plated onto LB plate, changed to a solid medium. 10 μl of culture filtrate was spread thereon, and cultured for 18 hours at 37□ (0.7% agar was used as "top-agar", and the titration of phage lysate was performed on the top-agar, called soft agar overlay method).

The sample culture medium containing the phage lysate was diluted, and mixed with 150 μl of ST shaking culture medium ($OD_{600}$=2), followed by soft agar overlay method, so that single plaques were obtained. Since a single plaque represents one bacteriophage, in order to isolate single bacteriophages, one plaque was added to 400 μl of SM solution (NaCl, 5.8 g; $MgSO_4 7H_2O$, 2 g; 1 M Tris-Cl (pH7.5), 50 ml; $H_2O$, final volume to 1 L), and left for 4 hours at room temperature to isolate single bacteriophages. To purify the bacteriophage in large quantities, 100 μl of supernatant was taken from the single bacteriophage solution, and mixed with 12 ml of 0.7% agar and 500 μl of ST shaking culture medium, followed by soft agar overlay method on LB plate (150 mm diameter). When lysis was completed, 15 ml of SM solution was added to the plate. The plate was gently shaken for 4 hours at room temperature to elute the bacteriophages from the top-agar. The SM solution containing the eluted bacteriophages was recovered, and chloroform was added to 1% of a final volume, mixed well for 10 minutes. The solution was centrifuged at 4000 rpm for 10 minutes. The obtained supernatant was filtered using a 0.2 μm filter, and stored in the refrigerator.

1-2. Large-Scale Batches of Bacteriophage

The selected bacteriophages were cultured in large quantities using ST. ST was shaking-cultured, and an aliquot of $1.5×10^{10}$ cfu (colony forming unit) was centrifuged at 4000 rpm for 10 minutes, and the pellet was resuspended in 4 ml of SM solution. The bacteriophage of $7.5×10^7$ pfu (plaque forming unit) was inoculated thereto (MOI: multiplicity of infection=0.005), and left at 37□ for 20 minutes. The solution was inoculated into 150 ml of LB media, and cultured at 37□ for 5 hours. Chloroform was added to 1% of a final volume, and the culture solution was shaken for 20 minutes. DNase I and RNase A were added to a final concentration of 1 μg/ml, respectively. The solution was left at 37□ for 30 minutes. NaCl and PEG (polyethylene glycol) were added to a final concentration of 1 M and 10% (w/v), respectively and left at 4□ for additional 3 hours. The solution was centrifuged at 4□ and 12000 rpm for 20 minutes to discard the supernatant. The pellet was resuspended in 5 ml of SM solution, and left at room temperature for 20 minutes. 4 ml of chloroform was added thereto and mixed well, followed by centrifugation at 4□ and 4000 rpm for 20 minutes. The supernatant was filtered using a 0.2 μm filter, and the bacteriophage was purified by glycerol density gradient ultracentrifugation (density: 40%, 5% glycerol at 35,000 rpm and 4 for 1 hour). The purified bacteriophage was designated as Bacteriophage ΦCJ2, and resuspended in 300 μl of SM solution, followed by titration. The bacteriophage ΦCJ2 was deposited at the Korean Culture Center of Microorganisms (361-221, Honje 1, Seodaemun, Seoul) on Dec. 17, 2008 under accession number KCCM10976P.

Example 2

Examination on ΦCJ2 Infection of *Salmonella*

To examine the lytic activity of the selected bacteriophages on other Salmonella species as well as ST, cross-infection attempts with other *Salmonella* species were made. As a result, ΦCJ2 did not infect SE (*Salmonella enterica Serotype Enteritis*), SC (*Salmonella enterica Serotype Choleraesuis*), SD (*Salmonella enterica Serotype Derby*) and SA (*Salmonella enterica* subsp. *Arizonae*), SB (*Salmonella enterica* subsp. *Bongori*). When cross-infection attempts were made with *Salmonella* species other than ST ATCC14028 strain, the lytic activity was 40% or less, unlike SG and SP. This result suggests that ΦCJ2 is a bacteriophage specific to SG and SP (see Example 11). The results are shown in the following Table 1. The bacteriophages ΦCJ2 that was produced using SG as a host cell showed the same plaque size and plaque turbidity, and the same protein patterns and genome size as those produced using ST as a host cell.

TABLE 1

<ɸCJ2 infection of *Salmonella*>

| Sero type | Strain name | Plaque formation | Sero type | Strain name | Plaque formation |
|---|---|---|---|---|---|
| SG | SGSC 2293 | ◯ | SC | ATCC 13312 | X |
| SP | SGSC 2295 | ◯ | SD | SCSG 2467 | X |
| ST | ATCC 14028 | ◯ | SA | ATCC 13314 | X |
| SE | SGSC 2282 | X | SB | ATCC 43975 | X |

ATCC: The Global Bioresource Center
SGSC: *salmonella* genetic stock center

Example 3

Morphology Examination of Bacteriophage ΦCJ2

The purified ΦCJ2 was diluted in 0.01% gelatin solution, and then fixed in 2.5% glutaraldehyde solution. After the sample was dropped onto a carbon-coated mica plate (ca.2.5× 2.5 mm) and adapted for 10 minutes, it was washed with sterile distilled water. Carbon film was mounted on a copper grid, and stained with 4% uranyl acetate for 30~60 seconds, dried, and examined under JEM-1011 transmission electron microscope (80 kV, magnification of ×120,000~×200,000). As a result, the purified ΦCJ2 was revealed to have morphological characteristics including an isometric capsid and a long non-contractile tail, as shown in <FIG. 1>, indicating that it belongs to the morphotype of the family Siphoviridae.

Example 4

Protein Pattern Analysis of Bacteriophage ΦCJ2

15 μl of purified ΦCJ2 solution ($10^{11}$ pfu/ml titer) was treated with 3 μl of 5×SDS sample solution, and heated for 5 minutes. The total protein of ΦCJ2 was run in 4-12% NuPAGE Bis-Tris gel (Invitrogen), and then the gel was stained with coomassie blue for 1 hour at room temperature. As shown in <FIG. 2>, the protein patterns showed that a band of approximately 40 kDa was observed as a major protein, and bands of approximately 65 kDa, 17 kDa, and 15 kDa were also observed.

Example 5

Total Genomic DNA Size Analysis of Bacteriophage ΦCJ2

Genomic DNA was isolated from the purified ΦCJ2 by ultracentrifugation. Specifically, to the purified ΦCJ2 culture medium, EDTA (ethylenediaminetetraacetic acid (pH8.0)), proteinase K, and SDS (sodium dodecyl sulfate) were added to a final concentration of 20 mM, 50 μg/ml, and 0.5% (w/v), respectively and left at 50□ for 1 hour. An equal amount of phenol (pH8.0) was added and mixed well, followed by centrifugation at 12000 rpm and room temperature for 10 minutes. The supernatant was mixed well with an equal amount of PC (phenol:chloroform=1:1), followed by centrifugation at 12000 rpm and room temperature for 10 minutes. The supernatant was mixed well with an equal amount of chloroform, followed by centrifugation at 12000 rpm and room temperature for 10 minutes. Again, to the supernatant, added were 1/10 volume of 3 M sodium acetate and two volumes of cold 95% ethanol, and left at −20□ for 1 hour. After centrifugation at 0□ and 12000 rpm for 10 minutes, the supernatant was completely removed, and the DNA pellet was dissolved in 50 μl TE (Tris-EDTA (pH 8.0)). The extracted DNA was diluted 10-fold, and its absorbance was measured at $OD_{260}$. After loading 1 μg of total genomic DNA in 1% PFGE (pulse-field gel electrophoresis) agarose gel, electrophoresis was performed using a BIORAD PFGE system program 7 (size range 25-100 kbp; switch time ramp 0.4-2.0 seconds, linear shape; forward voltage 180 V; reverse voltage 120 V) at room temperature for 20 hours. As shown in <FIG. 3>, ΦCJ2 had a genomic DNA size of approximately 43 kbp.

Example 6

Genetic Analysis of Bacteriophage ΦCJ2

To analyze genetic features of the purified ΦCJ2, 5 μg of genomic DNA of ΦCJ2 was treated with the restriction enzyme EcoR V. The vector pCL (Promega) was digested with Sma I, and treated with CIP (calf intestinal alkaline phosphatase). The digested genomic DNA and vector were mixed in a ratio of 3:1, and ligated at 16□ for 5 hours. The ligation product was transformed into *E. coli* DH5α. The transformed cells were plated on LB plate containing spectinomycin and X-gal (5-bromo-4-chloro-3-indolyl-beta-D-galactopyranoside) for blue/white selection, so as to select three colonies. The selected colony was shaking-cultured in a culture medium containing spectinomycin for 16 hours. Then, plasmids were extracted using a plasmid purification kit (Promega). The cloning of the plasmids was confirmed by PCR using a primer set of M13 forward and M13 reverse, and insertion fragments of 1 kbp or more were selected, and their base sequence was analyzed using the primer set of M13 forward and M13 reverse. As shown in SEQ ID NOs. 1, 2 and 3, the size was approximately 3.1 kbp, 1.7 kbp and 800 bp, respectively. Sequence similarity was analyzed using a NCBI blastx program, and the results are shown in the following Table 2.

As shown in the following Table 2, ΦCJ2 showed 90% sequence similarity with BPKS7gp07 of salmonella phage KS7 and with the coat protein of SETP3 in the forward sequence of SEQ ID NO. 1. The backward sequence of SEQ ID NO. 1 also showed 75% and 66% sequence similarity with BPKS7gp04 and SPSV3_gp41 of *salmonella* phage KS7 and phage SET3, respectively. In SEQ ID NO. 2, the forward sequence showed 91% sequence similarity with the hypothetical protein SPSV3_gp02 of salmonella phage SETP3, and the backward sequence showed 94% sequence similarity with the tail component protein of salmonella phage SETP3. The sequence of SEQ ID NO. 3 also showed 69% sequence similarity with BPKS7gp41 of salmonella phage KS7 and DNA polymerase of phage SETP3. The base sequence analysis of SEQ ID NOs. 1 2 and 3 by NCBI blastn program resulted in 60-70% sequence similarity with salmonella phage KS7 and SETP3. However, they are not completely identical to each other, suggesting that ΦCJ2 is a novel bacteriophage that infects *salmonella*.

of bacteriophage and 0.5 pmol of primer were added to premix (Bioneer), and the final volume was adjusted to 20 μl. PCR was performed with 30 cycles of denaturation; 94☐ 1 min, annealing; 53☐ 1 min, and polymerization; 72☐, 1 min. When SEQ ID NOs. 4 and 5, SEQ ID NOs. 6 and 7, and SEQ ID NOs. 8 and 9 were used as primer set, all PCR products had a size of approximately 1 kbp. The results are shown in <FIG. 4>.

Example 8 pH Stability Test on Bacteriophage

To test the stability of ΦCJ2 in a low-pH environment like the chicken stomach, the stability test was performed in a wide range of pH (pH 2.1, 2.5, 3.0, 3.5, 4.0, 5.5, 6.4, 6.9, 7.4, 8.2, 9.0). Various pH solutions (Sodium acetate buffer (pH 2.1, pH 4.0, pH 5.5, pH 6.4)), Sodium citrate buffer (pH 2.5, pH 3.0, pH 3.5), Sodium phosphate buffer (pH 6.9, pH 7.4), Tris-HCl (pH 8.2, pH 9.0)) were prepared at a concentration of 2 M. 100 μl of pH solution was mixed with an equal amount of bacteriophage solution ($1.0 \times 10^{11}$ pfu/ml) to the concentration of each pH solution to 1 M, and left at room temperature for 1 hour. The reaction solution was serially diluted, and 10 μl of each diluted sample was cultured at 37☐ for 18 hours by soft agar overlay method, and the titration of phage lysates was performed. Changes in the titers according to pH difference were compared to examine the relative stability. The results showed that the bacteriophage did not lose its infec-

TABLE 2

<Sequence similarity comparison of φCJ2 with other bacteriophages>

| | organism | protein | Accession number | Subject location | Query location | identities | E value |
|---|---|---|---|---|---|---|---|
| 1 | *Salmonella* phage KS7 | hypothetical protein BPKS7gp09 | AAW51212 | 123-349 | 3-683 | 205/227 (90%) | 7e-115 |
| | *Salmonella* phage SETP3 | putative coat protein | ABN47366 | 123-349 | 3-683 | 203/227 (89%) | 6e-114 |
| | *Salmonella* phage SETP3 | hypothetical protein SPSV3_gp41 | ABN47370 | 1-169 | 1630-2136 | 112/169 (66%) | 1e-49 |
| | *Salmonella* phage KS7 | hypothetical protein BPKS7gp04 | AAW51207 | 1-199 | 2142-2747 | 153/202 (75%) | 2e-79 |
| 2 | *Salmonella* phage KS7 | hypothetical protein | AAW51256 | 1-433 | 372-1670 | 402/433 (92%) | 0.0 |
| | *Salmonella* phage SETP3 | tail component protein | ABN47332 | 9-322 | 729-1670 | 296/314 (94%) | 5e-164 |
| | Bacteriophage MB78 | hypothetical protein | CAB36893 | 21-287 | 3-803 | 248/267 (92%) | 3e-143 |
| | *Salmonella* phage SETP3 | hypothetical protein SPSV3_gp02 | ABN47331 | 21-267 | 3-743 | 225/247 (91%) | 6e-129 |
| 3 | *Salmonella* phage KS7 | hypothetical protein BPKS7gp41 | AAW51246 | 176-417 | 789-1 | 182/263 (69%) | 1e-87 |
| | *Salmonella* phage SETP3 | DNA polymerase | ABN47339 | 176-417 | 789-1 | 182/263 (69%) | 2e-87 |

Example 7

Construction of ΦCJ2-Specific Primer Sequence

To identify ΦCJ2, ΦCJ2-specific primers were constructed on the basis of SEQ ID NOs. 1, 2 and 3. PCR was performed using each primer set of SEQ ID NOs. 4 and 5, SEQ ID NOs. 6 and 7, and SEQ ID NOs. 8 and 9. 0.1 μg of genomic DNA tivity and maintained stability to pH 2.5. However, it lost its infectivity at pH 2.1. The results are shown in <FIG. 5>

Example 9

Heat Stability Test on Bacteriophage

To test stability of bacteriophage to heat generated during formulation process when used as a feed additive, the following experiment was performed. 200 μl of ΦCJ2 solution (1.0×$10^{11}$ pfu/ml) was left at 37°C, 45°C, 53°C, 60°C, 70°C, and 80°C for 0 min, 10 min, 30 min, 60 min, and 120 min, respectively. The solution was serially diluted, and 10 μl of each diluted sample was cultured at 37°C for 18 hours by soft agar overlay method, and the titration of phage lysates was performed. Changes in the titers according to temperature and exposure time were compared to examine the relative stability. The results showed that the bacteriophage retained its infectivity following incubation at 60°C for 2 hours. However, the bacteriophage rapidly lost its infectivity following incubation at 70°C or higher for 10 minutes. The results are shown in <FIG. 6>.

Example 10

Dry Stability Test on Bacteriophage

To test stability of bacteriophage under the dry condition during formulation process when used as a feed additive, the following experiment was performed. On the basis of the results of heat stability test, the experiment was performed under high-temperature drying conditions (at 60°C for 120 min). 200 μl of ΦCJ2 solution (1.0×$10^{11}$ pfu/ml) was dried using a Speed vacuum (Speed—Vacuum Concentrator 5301, Eppendorf). The obtained pellet was completely resuspended in an equal amount of SM solution at 4°C for one day. The solution was serially diluted, and 10 μl of each diluted sample was cultured at 37°C for 18 hours by soft agar overlay method, and the titration of phage lysates was performed. Changes in the titers before and after drying were compared to examine the relative stability. The results showed that its activity was not reduced. The results are shown in <FIG. 7>.

Example 11

Examination on Bacteriophage Infection of Wild-Type Strain

The lytic activity of bacteriophage ΦCJ2 was tested for each 20 strains of the Korean wild-type SG and SP, isolated by Laboratory of Avian Diseases, College of Veterinary Medicine, Seoul National University, in addition to SG (SG SGSC2293), SP (SP SGSC2295) and ST (ST ATCC14028) used in the present invention. 150 μl of each strain shaking culture medium ($OD_{600}$=2) was mixed, and 10 μl of ΦCJ2 solution ($10^{10}$ pfu/ml) was cultured at 37°C for 18 hours by soft agar overlay method, and the plaque formation was examined. It was found that the bacteriophage ΦCJ2 showed 100% lytic activity on the wild-type SG and SP. The results are shown in the following Table 3. Its lytic activity on 20 strains of wild-type ST was also examined, revealing that the bacteriophage ΦCJ2 showed 80% lytic activity (not shown in the following Table 3). Thus, the results suggest that ΦCJ2 is a bacteriophage being specific to SG, SP and ST.

TABLE 3

<Lytic activity on wild-type SG, SP and ST>

| Sero type | Strain name | plaque formation | Sero type | Strain name | plaque formation | Sero type | Strain name | plaque formation |
|---|---|---|---|---|---|---|---|---|
| SG | SNU SG1 | ○ | ST | SNU ST1 | X | SP | SNU SP1 | ○ |
| | SNU SG2 | ○ | | SNU ST2 | ○ | | SNU SP 4 | ○ |
| | SNU SG3 | ○ | | SNU ST3 | X | | SNU SP 5 | ○ |
| | SNU SG4 | ○ | | SNU ST4 | ○ | | SNU SP 8 | ○ |
| | SNU SG5 | ○ | | SNU ST7 | ○ | | SNU SP 11 | ○ |
| | SNU SG6 | ○ | | SNU ST8 | ○ | | SCSG 2294 | ○ |
| | SNU SG7 | ○ | | SNU ST11 | ○ | | SCSG 2295 | ○ |
| | SNU SG8 | ○ | | SNU ST12 | ○ | | SCSG 2737 | ○ |
| | SNU SG9 | ○ | | SNU ST13 | ○ | | SCSG 2739 | ○ |
| | SNU SG10 | ○ | | SNU ST14 | ○ | | SCSG 2742 | ○ |
| | SNU SG11 | ○ | | SNU ST17 | ○ | | SCSG 2743 | ○ |
| | SNU SG12 | ○ | | SNU ST18 | X | | SCSG 2745 | ○ |
| | SNU SG13 | ○ | | SNU ST19 | ○ | | SCSG 2751 | ○ |
| | SNU SG14 | ○ | | SNU ST20 | ○ | | SCSG 4663 | ○ |
| | SNU SG15 | ○ | | SNU ST25 | ○ | | SCSG 4664 | ○ |
| | SCSG 9184 | ○ | | SNU ST26 | ○ | | SCSG 4665 | ○ |
| | SCSG 2292 | ○ | | SNU ST37 | ○ | | SCSG 4666 | ○ |
| | SCSG 2293 | ○ | | SNU ST38 | X | | SCSGSA1684 | ○ |

TABLE 3-continued

<Lytic activity on wild-type SG, SP and ST>

| Sero type | Strain name | plaque formation | Sero type | Strain name | plaque formation | Sero type | Strain name | plaque formation |
|---|---|---|---|---|---|---|---|---|
| | SCSG 2744 | ○ | | SNU ST41 | ○ | | | |
| | SCSG 2296 | ○ | | SNU ST42 | ○ | | | |

SG/SP source: Laboratory of Avian Diseases, College of Veterinary Medicine, Seoul National University
SGSC: *salmonella* genetic stock center

Example 12

Toxicity Test of Bacteriophage

To evaluate ΦCJ2 safety in rats, toxicity studies were performed. Single dose oral and intravenous toxicity studies and toxicity study on normal enteric bacteria were performed.

To examine acute toxicity in rats and mortality rate by single oral administration, single dose oral toxicity study was performed. Male and female (12 rats for each), 7-week-old, specific pathogen-free (SPF) rats were fasted one day before ΦCJ2 administration. On administration day, $1 \times 10^{12}$ pfu of ΦCJ2 was administered to male and female rats (6 rats for each) via an oral zonde, and a mixed solution of 20 mM Tris-HCl and 2 mM $MgCl_2$ was orally administered to 6 rats as a control group, after 4 hrs, to start refeeding. On administration day, the rats were examined 30 min after administration, and every 4 hours. For 14 days, clinical signs were examined and recorded once a day. As a result, there was no animal death, and clinical signs due to ΦCJ2 toxicity were not observed. The results are shown in Tables 4 and 5. Changes in body weight were measured and recorded before administration, and 1, 3, 7, 10 and 14 days after administration. As shown in FIG. 8, there were no significant changes in body weight, as compared to control group. The results indicate that ΦCJ2 does not induce loss of appetite or toxic signs which cause changes in body weight. The surviving rats were autopsied and examined for gross lesions. No gross abnormalities were observed.

TABLE 5-continued

<Clinical signs after oral administration of ΦCJ2>

| | Dose | Final mortality | | Clinical signs | |
|---|---|---|---|---|---|
| Sex | (pfu) | Male | Female | Male | Female |
| Female | Control | 0/6 | 0/6 | 0/6 | 0/6 |
| | $1 \times 10^{12}$ | 0/6 | 0/6 | 0/6 | 0/6 |

[a]Values are expressed as number of dead animal/total number of animals.
[b]Values are expressed as number of animals with clinical signs/total number of animals.

To examine bacteriophage toxicity in blood, single dose intravenous toxicity study was performed. Male and female (10 rats for each), 7-week-old, specific pathogen-free (SPF) rats were subjected to the experiment. On administration day, $1 \times 10^{12}$ pfu of ΦCJ2 was administered to the lateral tail veins of male and female rats (5 rats for each) using a 3 ml syringe, and a mixed solution of 20 mM Tris-HCl and 2 mM $MgCl_2$ was administered into the lateral tail veins of 5 rats as a control group. Under the same conditions as oral toxicity study, animal death and clinical signs, changes in body weight and the result of necropsy were examined, and shown in Tables 6 and 7, and FIG. 9, respectively. During the experimental period, there was no animal death, and clinical signs due to ΦCJ2 toxicity were not observed. Further, there were no significant changes in body weight, as compared to control group. The results indicate that ΦCJ2 does not induce toxicity. Furthermore, the surviving rats were autopsied and examined for gross lesions. No gross abnormalities were observed.

TABLE 4

<Incidence of death after oral administration of ΦCJ2>

| sex | Dose (pfu) | Hours after treatment | | | | | Days after treatment | | | | | | | | | | | | | | Final mortality |
|---|---|---|---|---|---|---|---|---|---|---|---|---|---|---|---|---|---|---|---|---|---|
| | | 0.5 | 1 | 2 | 3 | 4 | 1 | 2 | 3 | 4 | 5 | 6 | 7 | 8 | 9 | 10 | 11 | 12 | 13 | 14 | |
| Male | Control | 0 | 0 | 0 | 0 | 0 | 0 | 0 | 0 | 0 | 0 | 0 | 0 | 0 | 0 | 0 | 0 | 0 | 0 | 0 | 0/6 |
| | $1 \times 10^{12}$ | 0 | 0 | 0 | 0 | 0 | 0 | 0 | 0 | 0 | 0 | 0 | 0 | 0 | 0 | 0 | 0 | 0 | 0 | 0 | |
| Female | Control | 0 | 0 | 0 | 0 | 0 | 0 | 0 | 0 | 0 | 0 | 0 | 0 | 0 | 0 | 0 | 0 | 0 | 0 | 0 | 0/6 |
| | $1 \times 10^{12}$ | 0 | 0 | 0 | 0 | 0 | 0 | 0 | 0 | 0 | 0 | 0 | 0 | 0 | 0 | 0 | 0 | 0 | 0 | 0 | |

TABLE 5

<Clinical signs after oral administration of ΦCJ2>

| | Dose | Final mortality | | Clinical signs | |
|---|---|---|---|---|---|
| Sex | (pfu) | Male | Female | Male | Female |
| Male | Control | 0/6[a] | 0/6 | 0/6[b] | 0/6 |
| | $1 \times 10^{12}$ | 0/6 | 0/6 | 0/6 | 0/6 |

TABLE 6

<Incidence of death after intravenous administration of ΦCJ2>

| sex | Dose (pfu) | Hours after treatment | | | | | Days after treatment | | | | | | | | | | | | | | Final mortality |
|---|---|---|---|---|---|---|---|---|---|---|---|---|---|---|---|---|---|---|---|---|---|
| | | 0.5 | 1 | 2 | 3 | 4 | 1 | 2 | 3 | 4 | 5 | 6 | 7 | 8 | 9 | 10 | 11 | 12 | 13 | 14 | |
| Male | Control | 0 | 0 | 0 | 0 | 0 | 0 | 0 | 0 | 0 | 0 | 0 | 0 | 0 | 0 | 0 | 0 | 0 | 0 | 0 | 0/5 |
| | $1 \times 10^{12}$ | 0 | 0 | 0 | 0 | 0 | 0 | 0 | 0 | 0 | 0 | 0 | 0 | 0 | 0 | 0 | 0 | 0 | 0 | 0 | |
| Female | Control | 0 | 0 | 0 | 0 | 0 | 0 | 0 | 0 | 0 | 0 | 0 | 0 | 0 | 0 | 0 | 0 | 0 | 0 | 0 | 0/5 |
| | $1 \times 10^{12}$ | 0 | 0 | 0 | 0 | 0 | 0 | 0 | 0 | 0 | 0 | 0 | 0 | 0 | 0 | 0 | 0 | 0 | 0 | 0 | |

TABLE 7

<Clinical signs after intravenous administration of ΦCJ2>

| | Dose | Final mortality | | Clinical signs | |
|---|---|---|---|---|---|
| Sex | (pfu) | Male | Female | Male | Female |
| Male | Control | 0/5[a] | 0/5 | 0/5[b] | 0/5 |
| | $1 \times 10^{12}$ | 0/5 | 0/5 | 0/5 | 0/5 |
| Female | Control | 0/5 | 0/5 | 0/5 | 0/5 |
| | $1 \times 10^{12}$ | 0/5 | 0/5 | 0/5 | 0/5 |

[a]Values are expressed as number of dead animal/total number of animals.
[b]Values are expressed as number of animals with clinical signs/total number of animals.

To examine the ΦCJ2 toxicity on normal enteric bacteria, 9 species of normal enteric bacteria, identified in toxicity test guidelines for animal drugs, (*Bacteroides fragilis* (ATCC25285), *Bacteroides ovatus* (ATCC8483), *Fusobacterium prausnitzii* (ATCC 27766), *Bifidobacterium Longum* (KACC 20597, ATCC15697), *Clostridium perfringens* (ATDD13124), *Peptococcus anaerobius* (ATCC27337), *Enterococcus faecalis* (KACC 11304, ATCC35308), *Lactovacillus acidophilus* (KACC12419, ATCC 4356), *Escherichia coli* (KACC 10005, ATCC 35607)) were subjected to the toxicity study. $1 \times 10^{11}$ pfu/ml of ΦCJ2 were serially diluted and 100 μl of dilution was aliquoted to a 96 well plate. Then, culture media of 9 species were added to the plate, and cultured under the predetermined conditions for 18~48 hrs. Cell density was measured to determine the minimal inhibitory concentration. It was found that the growth of enteric bacteria was not inhibited even at the maximum concentration of ΦCJ2, shown in Table 8. The results indicate that ΦCJ2 does not affect normal enteric bacteria.

TABLE 8

| Microorganism | Media | Culture conditions | ΦCI2 | MIC |
|---|---|---|---|---|
| *Bacteroides fragilis* (ATCC 25285) | Thioglycollate anaerobic | 37° C. Strict anaerobic (GasPak) | $1 \times 10^2 \sim 1 \times 10^{10}$ CFU/ml by 10-fold dilution | Not determined (ND) |
| *Bacteroides ovatus* (ATCC 8483) | Thioglycollate anaerobic | 37° C. Strict anaerobic (GasPak) | | ND |
| *Fusobcterium preusnitzii* (ATCC 27766) | Thioglycollate anaerobic | 37° C. Strict anaerobic (GasPak) | | ND |
| *Bifidobacterium Longum* (KACC 20597, ATCC 15697) | Reinforced clostridial medium anaerobic | 37° C. Strict anaerobic (GasPak) | | ND |
| *Clostridium perfringens* (ATCC 13124) | Reinforced clostridial medium anaerobic | 37° C. Strict anaerobic (GasPak) | | ND |
| *Peptococcus anaerobius* (ATCC 27337) | Thioglycollate anaerobic | 37° C. Strict anaerobic (GasPak) | | ND |
| *Enterococcus faecalis* (KACC 11304, ATCC 35308) | Muller Hinton Broth | 37° C. aerobic | | ND |
| *Lactobacillus acidophilus* (KACC 12419, ATCC 4356) | Lactobacilli MRS Broth | 37° C. 5% $CO_2$ (GasPak) | | ND |
| *Escherichia coli* (KACC 10005, ATCC 35607) | Muller Hinton broth | 37° C. aerobic | | ND |

Example 13

Efficacy Test on Bacteriophage

In order to evaluate the efficacy of ΦCJ2 on the prevention and treatment of ST, SG and SP, efficacy test was performed in chickens.

20 brown layers (1-day-old) were divided into 10 test groups with 10 layers (ΦCJ2 treated group+non-treated challenged group 1). For 1 week, the test chicks were fed with feed supplemented with $10^7$ pfu of ΦCJ2 (per g) and drinking water supplemented with $10^7$ pfu of ΦCJ2 (per ml). At 1 week, $10^6$ cfu of SG0197 (per chick) and $10^7$ pfu (MOI=10) of each phage were mixed with 500 μl of TSB, and left in ice for 1 hour or less, followed by oral administration. The mortality rate was examined for 2 weeks. The surviving chicks were subjected to necropsy and examined for gross lesions, and the bacteria were isolated. As shown in <Table 9>, it was found that the ΦCJ2-treated group showed a significantly higher protection rate ($P<0.05$) than the non-treated group.

TABLE 9

<Efficacy test of ΦCJ2 in chickens>

|  | ΦCJ2-treated challenged group | Non-treated challenged group |
|---|---|---|
| Survival | 9 | 3 |
| Mortality rate | 10% | 70% |
| Clinical signs | 1/9 | 1/3 |
| SG reisolation | 0/9 | 0/3 |
| Protection rate | 80% | 20% |

INDUSTRIAL APPLICABILITY

The bacteriophage of the present invention has a specific bactericidal activity against *Salmonella typhimurium*, *Salmonella gallinarum* and *Salmonella Pullorum* without affecting beneficial bacteria, and excellent acid-, heat- and dry-resistance, and thus can be applied to the compositions that can be used for the prevention or treatment of infectious diseases caused by *Salmonella typhimurium*, *Salmonella gallinarum* and *Salmonella pullorum*, in particular, salmonellosis, *Salmonella* food poisoning, Fowl typhoid, and Pullorum disease, and applied to therapeutics, antibiotics, animal feed, drinking water for animal, sanitizers, and cleaners.

The invention claimed is:

1. An isolated bacteriophage, which is deposited under accession number KCCM10976P, having a specific bactericidal activity against *Salmonella typhimurium, Salmonella gallinarum* or *Salmonella pullorum*.

2. A composition for the inhibition or treatment of infectious diseases caused by one or more selected from the group consisting of *Salmonella typhimurium, Salmonella gallinarum* and *Salmonella pullorum*, comprising the isolated bacteriophage of claim 1 as an active ingredient.

3. The composition according to claim 2, wherein the infectious disease caused by *Salmonella typhimurium* is salmonellosis or *Salmonella* food poisoning, the infectious disease caused by *Salmonella gallinarum* is Fowl typhoid, and the infectious disease caused by *Salmonella pullorum* is Pullorum disease.

4. An antibiotic composition comprising an isolated bacteriophage, which is deposited under accession number KCCM10976P, having a specific bactericidal activity against *Salmonella typhimurium, Salmonella gallinarum* or *Salmonella pullorum*.

5. An animal feed or drinking water, comprising the isolated bacteriophage of claim 1 as an active ingredient.

6. A sanitizer or cleaner, comprising the isolated bacteriophage of claim 1 as an active ingredient.

7. A method for treating infectious diseases caused by one or more selected from the group consisting of *Salmonella typhimurium, Salmonella gallinarum* and *Salmonella pullorum*, using the isolated bacteriophage of claim 1.

8. A method for treating infectious diseases caused by one or more selected from the group consisting of *Salmonella typhimurium, Salmonella gallinarum* and *Salmonella pullorum*, using the composition of claim 2.

* * * * *

```
SEQUENCE LISTING

<160> NUMBER OF SEQ ID NOS: 9

<210> SEQ ID NO 1
<211> LENGTH: 3083
<212> TYPE: DNA
<213> ORGANISM: Bacteriophage KCCM 10976P

<400> SEQUENCE: 1
tggataactt ctggcagcgc caggcacagc gtcgtctgat tgctaccgct ctcggcctgt    60
acaacgataa cgttgctgca accgacgaat accacaccca gaacgacatg gttatcgatg   120
tatccgccac catgggcttt gatgcgggtg cctttatcga cgccacccag actatgggcg   180
acgcgctgat gggctcaact ggtgaagtgc tcggtgctat tgcgatgcac agcttcgtgt   240
acggccaggc acgtaaagcc aacctgattg acttcatccg tgactccgaa aataacacca   300
tgtttgctac atatcagggc taccgcgtgg ttgttgatga tagcatgacc gttgtaggca   360
ccggtaatga ccgcaagttt atcagcatca ttttcggcaa cggcgcaatc ggctacggcg   420
aaggtactcc ggagaaccca ctggaatatg agcgtgaagc ctcacgcggt aacggcggcg   480
gtgttgaaac cctgtggacc cgtaaaacct ggctgctgca cccgctgggc tacagcttca   540
ctagcgcggt aatcaccggt aacggctccg aaaccatcgc ccgctccgct tcctggcagg   600
acctggcgaa cgccgccaac tggaatcgcg tagtagagcg caaacacgtt ccaatcgcgt   660
tcctggttac tggcgtaggc gcgtaacagt agcgtataat caggagggc tacggcccct   720 cttttcacat tcatacggga gaaatgtatg gcaccacag gtaaagggct gccacgcagt   780
ctgaaagacg ccaaactgaa catccctatg gcgactacat cggatgttgg tggcgtaaaa   840
```

| | |
|---|---|
| aagtcagcta ctgtagcctc gccagccgct attactgctg ccgcaggaac ccaatcagtc | 900 |
| gccgacccta ctaaggccga atttgatgca ctcgtggcgg agtacaacaa actccgaacc | 960 |
| gatgtcacag cgctgcgcac taccgtagca aacctgttaa ccgcgcttaa aaacgctgga | 1020 |
| actgtaagct aaaggagctt aaaaatggtt gatgtaatta aacgccgtat ggtaggcgtc | 1080 |
| tccgacgact cccctgctga tggtcaggta gaaatcgaca tggtaaacat ttccccagcg | 1140 |
| tcgttttcta caggcctgaa tgacactacg gcagtaaccg caccggcggc gctgacactc | 1200 |
| accgtagcgg cggcagggggg ccgagagcca tacagctatc agtggttcaa aaacggtaac | 1260 |
| gccatttctg gcgcaacggc ggcgacttac actaagacgc ctaccgttgc cacggttgat | 1320 |
| tccggcactt acaaagttgt tgcccaggat ggttatggta atatcatctc agacagcact | 1380 |
| attgtcacag tatcttaatt aaacggccct tcggggccgt cataggggaaa cataatggtt | 1440 |
| aatgacaatt acgtaatccg cgagaaatat aacggtctgg tagagattga cggccagctc | 1500 |
| gtaccacagc gcggaaatgt tctgccggaa gaactggtgg caacgcaacc ggataacgaa | 1560 |
| gaagcgcaca ataacggtgg cggcgccgag cctaaacgcc gtcgtcgtcg cacgttcgag | 1620 |
| gaataaccaa tggctttagt cgtcgaagat ggttctatag ttgcaggagc tgacagctat | 1680 |
| cttagcctgg aggacgcccg cgcactggcg gctaaatacg gctatgtgtt acccgctgag | 1740 |
| ggtaatgagg ctgaagccgc gctccgcaat ggtgcgatgt acgtcggttt acaagagcct | 1800 |
| gctatgtgtg gtcgtcgtgt atccgcgacg cagtccttat cgtttccgcg cactggaatt | 1860 |
| agtctgtacg gtttccctgt ggcgagtaat gttatcccgg accaggttaa actcgcgcag | 1920 |
| cttatcgctg gcgtagagta cggtaacggt gcggatgtgc gcgccagttc agacgggcgt | 1980 |
| gttacgacta tggagcgcgt agaaggtgcg gtgacagtac agtacgccaa caacggcaac | 2040 |
| accgggtcga caatcactat cacggcatct atggacgcat tacgcccgct gctgtgtggc | 2100 |
| tccaacaacg ctttctcttt taatgtttat cggggttaga gatggctaaa acgaagagtg | 2160 |
| aaatgtttgc gcttatcggg ggcaattttc cggataacac gaccggagcc atcacaccag | 2220 |
| aaaagctaag agaagtaaca acgcaactgg cagactctat gttgtatgct gccactggag | 2280 |
| tgaaagaggt ggaagtactg agggcctctt ctactgtcgc acaagcacca acggcagttg | 2340 |
| acactgcgtt acagttatct tttggcgcag ctcagggcgc ggcatctaac ccagttatga | 2400 |
| ttaacgcggc cggtcttgtt acgtttaaca ccgcgggtaa ttatgcggtt cgcatcaaat | 2460 |
| tacaggcggg gcgcacaggg gccagtggga cttctattct gttatcgcgc attcttgtga | 2520 |
| acgggtctca atacgttca cctgcggcta ccaagctagt aagcgcggac gttacgatac | 2580 |
| ctatagaatc ccgcgtcgtt attaacgctg ccgcagggca gactatggct gtgcagatta | 2640 |
| tgagagatag cgcaggcact aattttggcg gtgtatatcc gcagactgcg accgtagctg | 2700 |
| cgtggggcat cgctccgtct gcgttactcg tcatctcaag actggagccc gcctaatgag | 2760 |
| cactgctttc agcaagaaaa tgcagggcgt ggagacacgc ctgttaggca aatatggcag | 2820 |
| cactgtaacg ctggttcgcg ctggttctaa ggtctgggac gaaagccttg gcgaatacgt | 2880 |
| gcgacagcca gatactcaga ttcctcttac cgccgtcccg gtgccgatta acgcggggct | 2940 |
| tgtcaacgga actaccattc aggtgggggga tatggtggtg aaagcggact atagtgtgct | 3000 |
| gccgaagatg gaagataagg tagaattttc tggggagcaa tggtcagttg tcggtatcga | 3060 |
| gaagaaaatc gttaacgatg ata | 3083 |

<210> SEQ ID NO 2
<211> LENGTH: 1670
<212> TYPE: DNA

<213> ORGANISM: Bacteriophage KCCM 10976P

<400> SEQUENCE: 2

```
atcgggatac cccgatgaac ttcgttgtca ataatatacc ggatggagtg ccggtgcgtg      60
tctttatcga tgagataggc gaagacaacg atgttactga ggatttcgaa gcattgaaag     120
aagacgcaat ctttcatgtt gttgagtccg cgggtggcgg agctattaaa ggtgtcatga     180
agattttcag tgtagtttta aaaccactgg cgaagctttt gtccccttca gtaaaaggtg     240
cgtcgtcaaa cctcgctaac tcgcaagcag actcccccaa caacagtctt tctgaccgca     300
ataataaagc gcgtccctat gagcgtagct atgacatttg cgggacggtg caaacgatac     360
caaacaacct tatgtcaact tataaggtgt ttaacgcagc gggtcgcatt atagaatatg     420
gatactacga tgctggtaga ggttatcttg acatacaccc tgacgaaata acagacggtg     480
atacccgtgt atctgacatc acagggacat cagttgccgt ctacgcgccg tacacgtcac     540
cgaataacac ggcaacgccg caagtactgg ttggagaccc gatagagcag gggttatatc     600
tgactgtcga atcaaatgaa gtagacggcg tggttctgaa agcacaaaac ggacttggca     660
tctcgttttc ttacatgtcc ggataccctt cgttatccgg ttccaccggc actatatacg     720
acccgtcagg ggggtctgac ttctccggtg ttcttgtgcc gaatgatacg ttttctctcg     780
tatccgcctg gacaaataca gatgttgacc tttccggtgg tggttatcag gtaataagtg     840
tttccgaagg aactgttact ttcgtagtcc ccggtaatct tataagtaaa tggcaacaaa     900
tacagccggg ttcgtttttt cgtggagacg gcgaagcctc gttgcaaccg ataacacat     960
atgaaaaaac gttaactgat tgggtgtcca taaaccgaac tgaggtggaa cgtattgtcg    1020
ctaacatagc ggccgcaaac gggatgtata agacaatgg tcgttccaaa cgttggctt    1080
cggtaacagc agaaatacaa taccaacttc ttgacgaaaa tagcgtgccc tacggcccga    1140
tttacgcggc gcaaggaacc gtatccgggc gcacttctga ctataacggc gtgactatat    1200
acgcagattt acccgtagcg tctcgtgttc gcgtcagggc gaggagagta acagaccttg    1260
atttcaattt cgaaggctca gttgtcgacg aaataaccta cgttaacctg tacgggcaga    1320
ctagagacaa caccccacac tacggcaacc gaaccactgt gcactcaatg cgtaagcaga    1380
cgccgcgcgc tgccgaagtt aagcaacctc agttgcgcat gattgcgacc gagatggtat    1440
ataaatatct tgggaatgga gtgtttgagg atacgatgtc gcctaataac caggcagtcc    1500
aatcgttaat tcgcctcgca agggaccctg acgtcggcgg gctcgattta acagtaagga    1560
atatggataa gttgcttgct gtacaaaagg aaatagagga ttacttcggc gacaagcaag    1620
ccggagaatt ctgttacacc ttcgatgatt ataaaacaac gatgcaggat                1670
```

<210> SEQ ID NO 3
<211> LENGTH: 790
<212> TYPE: DNA
<213> ORGANISM: Bacteriophage KCCM 10976P

<400> SEQUENCE: 3

```
atcgaggcca gcttcgaagg tcgcaagagc cgtctttca ccagccagcc atgcaagacc       60
gcgcccttcc acgttggaat aatcggcaac cagtagctta ttaccgggtg taggcaccac     120
gcagctacga acagttgtgg ctgttaattt cgatacgtca taggcccagt gcgctcgacc     180
ttttagcagc atgtcaatgc cagttgatag cgcgtgctta cgcaacaggt aattacgctc     240
agactcaccg ggcatccgaa ttactttatc ctccgggtca tcatcgtaat agccacgagc     300
taagttctga ggctggaagc ctttacccgc aaaacgtaaa gtcctggacg ctccgccgta     360
```

```
ctggagacaa ccacgacgac gaccgtcggc ggacagacca agcaggagcg ggttgtactt      420
ggtcgatgcc gtggagctgg cccccagacg catttcgata agtgtacgag cgtcgtcagg      480
caggtcatcg tcagccagca agtcgtttag cgtggacttc tgcgcgttga gaatctcatg      540
acctggtgcg aggtctcgca gcgtaggcag aaaatcagca ccggtaagac ccgcgcccca      600
tttggcgttt gcttcagcct gtagttcaat cttgtgctgc ttcaccgcgt cgattgccgc      660
attagccagc gccgtgtcga cgtagaagcc gcggtcgttg atgcgctggt cgacagccag      720
gacggtgttc tcgaactcgg tgttgcccca ctgcggcagc gagtgataaa cctcgcgcat      780
agatgtgata                                                             790

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
aagacttcgc attataataa gtg                                               23

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
ttaaagtttg taactcgtac ac                                                22

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ccgaaactcc catgaataaa t                                                 21

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ttatagttct catcgtcgag                                                   20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cgcataactg ggttgcagga                                                   20

<210> SEQ ID NO 9
<211> LENGTH: 22
<212> TYPE: DNA
```

```
<213> ORGANISM: Artificial Sequence
<220> FEATURE:
<223> OTHER INFORMATION: primer

<400> SEQUENCE: 9
gagagtactg tgttgctatt ta                                              22
```